United States Patent [19]

Meletiou et al.

[11] Patent Number: 5,219,388
[45] Date of Patent: Jun. 15, 1993

[54] METHOD AND APPARATUS FOR TESTING WATER PERMEABILITY OF CONCRETE

[75] Inventors: Constantinos A. Meletiou; David G. Bloomquist; Mang Tia, all of Gainesville, Fla.

[73] Assignee: University of Florida, Gainesville, Fla.

[21] Appl. No.: 821,811

[22] Filed: Jan. 17, 1992

[51] Int. Cl.$^5$ .................. E21B 21/08; G01N 15/08
[52] U.S. Cl. .................................... 73/155; 73/38
[58] Field of Search ............... 73/153, 155, 38, 64.47, 73/861.49

[56] References Cited

U.S. PATENT DOCUMENTS

| | | | |
|---|---|---|---|
| 2,688,872 | 9/1954 | Hartline et al. | 73/155 |
| 3,035,440 | 5/1962 | Reed | 73/38 |
| 3,158,020 | 11/1964 | Donaldson | 73/38 |
| 3,184,957 | 5/1965 | Ellis et al. | 73/38 |
| 3,332,483 | 7/1967 | Wyllie | 73/155 |
| 3,388,586 | 6/1968 | Golmard et al. | 73/38 |
| 3,838,599 | 10/1974 | Purtell | 73/861.49 |
| 3,861,196 | 1/1975 | Domenighetti | 73/38 |
| 4,148,212 | 4/1979 | Torstensson | 73/38 |
| 4,353,249 | 10/1982 | Lagus et al. | 73/155 |
| 4,531,403 | 7/1985 | de Korompay et al. | 73/38 |
| 4,718,270 | 1/1988 | Storr | 73/38 |
| 4,854,157 | 8/1989 | Wilson | 73/38 |
| 4,979,390 | 12/1990 | Schupack et al. | 73/38 |

Primary Examiner—Hezron E. Williams
Assistant Examiner—George M. Dombroske
Attorney, Agent, or Firm—Kerkam, Stowell, Kondracki & Clarke

[57] ABSTRACT

A method for measuring the water permeability in a concrete structure comprising: (a) pressure sealing a selected length of a borehole in the concrete structure, (b) injecting an aqueous medium into the selected length of borehole, (c) applying sufficient pressure to the injected aqueous medium and for a time necessary to produce a substantially steady state, measurable flow of the aqueous medium into the concrete structure from the selected length of borehole, (d) measuring the steady state flow of aqueous medium, and (e) computing from the steady state flow measurement the water permeability of the concrete structure. An apparatus employing the method is also disclosed.

16 Claims, 6 Drawing Sheets

METHOD AND APPARATUS FOR TESTING WATER PERMEABILITY OF CONCRETE

BACKGROUND OF THE INVENTION

Research leading to the completion and reduction to practice of this invention was supported, in part, by the Florida Department of Transportation via Contract No. 3366.

1. Field of the Invention

The invention relates to a method and system for determining the permeability to water of concrete.

2. Discussion of the Prior Art

Reinforced and pre-stressed concrete structures are commonly used in the construction of roadways, bridges, buildings, pre-cast concrete elements and the like. Such concrete structures generally comprise reinforced steel embedments such as rods, mesh or cables which are enclosed in formed concrete. It has been found that such concrete structures tend to deteriorate, with cracking and spalling of the concrete, when corrosive ions permeate the concrete and cause the reinforcing steel to corrode. Ions such as chlorides are likely to be present where road de-icing salts are used, and in marine environments. The chloride ions tend to depassify the alkali components of the concrete, and cause corrosion of the reinforcing steel embedments. The corrosion products of the reinforcing steel have a larger volume than the original steel and, therefore, create internal pressures in the concrete structure that causes it to crack and spall.

A related problem is the carbonation of the concrete structure. Carbonation occurs when carbon dioxide and carbon monoxide, from the exhaust of an internal combustion engine or the atmosphere, permeate the concrete and react with the hydrated cement compounds forming calcium carbonate. This tends to neutralize the alkaline environment surrounding the steel embedment, making the steel vulnerable to corrosion if moisture and oxygen are available.

Unwanted excessive permeability can occur in all concrete because of poor mix design, e.g., excessive water content, lack of fines or excessive air entrapment, or because of inadequate or inconsistent consolidation or due to poor finishing of the concrete. In addition to being susceptible to corrosion of the steel embedments, concrete having a high permeability tends to have a lower compressive and tensile strength and lessened durability and abrasion resistance than concretes of low permeability.

Corrosion problems also arise because of water and chloride ions leakage through joints in the concrete. Leakage through joints, as opposed to permeation through the concrete matrix, can occur in caulked joints such as flexible joints located between slabs of concrete. Leakage can also occur in cold joints which are joints between portions of a concrete structure which are cast at different times so that the concrete matrix loses continuity. Another location where water leakage problems frequently arise is in anchors for post-tensioning tendons which are typically sealed with a cement mortar patch after post-tensioning.

Sealers such as silane and siloxane solutions are often applied to the concrete and masonry to reduce the permeability and leakage of the structures. However, sealers tend to erode with time, thus reducing their effectiveness as barriers to ion intrusion. In addition, a sealer may not be properly or evenly applied to a structure so that the protection against weathering and ion intrusion varies over the surface of the structure.

Concrete formulations which have low absorption and low permeability have also been developed; however, these formulations are dependent on proper formulation, installation and curing for their effectiveness, and it is desirable to have quality control mechanisms even when these concrete formulations are employed.

In evaluating the permeability characteristics of concrete and masonry, there are three main elements which determine the overall permeability of the structure. These are: (1) leakage through joints and cracks, (2) surface permeability, and (3) matrix permeability. Where there are joints and cracks in the structure, these may be the major sources of liquid and ion penetration into the structure and may dominate any measure of the overall permeability of a structure.

In continuous, undamaged concrete, the surface permeability may be the limiting factor in the overall liquid and ion permeability, for example, in a low density concrete having a properly applied sealer. In other concrete structures, the matrix permeability may be the limiting factor, for example, in a high density concrete with a poor finish.

Several in situ tests of permeability have been proposed. U.S. Pat. No. 3,184,957 discloses an apparatus which comprises a series of reservoirs which, by the displacement of liquid from one reservoir to another, provide a stream of air or vapor to a dome placed on asphalt paving being tested. The degree of permeability is determined by measuring the time required to displace a fixed volume of liquid or the amount of liquid displaced in a fixed time. In an alternative embodiment, a slight vacuum is provided in the dome by the displacement of liquid.

U.S. Pat. No. 4,531,403 describes a system involving the use of a straddle packer and the application of negative fluid pressure to a sealed area to test for cracks and faults in structures such as mine roofs and the like.

U.S Pat. No. 3,861,196 discloses an apparatus having a central liquid chamber having an open end surrounded by an annular chamber in which a pressurized bladder seals the central chamber. The chambers are placed against the structure to be tested, and a liquid is provided under pressure to the central chamber. The flow rate of the liquid into the central chamber provides a measure of the permeability of the structure.

U.S. Pat. No. 4,979,390 describes a system for measuring the surface permeability of concrete comprising an apparatus for sealing a head chamber against the surface of a concrete structure, means for applying a partial vacuum to the head chamber and a pressure gauge for measuring pressure differences in the head chamber.

A report by the Concrete Society entitled "Permeability Testing of Site Concrete—A Review of Methods and Experience" describe the Figg method of determining permeability in which a hypodermic needle is sealed into a hole in a concrete structure and a vacuum is provided in the needle. The pressure increase is measured to provide a measure of the air permeability of the concrete. The Concrete Society report also describes the initial surface absorption test (ISAT) in which liquid absorption of concrete is tested using a cap which is mechanically attached to the surface of a structure and into which water is fed from a reservoir. These test apparatii and methods suffer from the need for mechanical attachment such as bolting or gluing of the test equipment to the structure so as to obtain a good seal between the cap and the concrete.

A paper by K. Schonlin and H.K. Hilsdorf entitled "Permeability as a Measure of Potential Durability of Concrete—Development of a Suitable Test Apparatus" (undated) describes a test apparatus for testing permeability of prepared samples of concrete in the laboratory. A concrete disk is cast in an air-tight rubber ring. A test apparatus, having a vacuum pump connected to a vacuum chamber located over the concrete disk, measures permeability based on the pressure increase in the vacuum chamber after the vacuum pump is isolated from the vacuum chamber.

It is desirable to provide an in situ method and apparatus for testing the permeability of the surface of concrete structures which, in addition to testing permeability, allows the tester to identify flaws in the structure which contribute to the permeability so that appropriate repairs may be made as necessary. In addition, it is desirable to provide a method and apparatus which is easily portable and which may be rapidly set up for testing. In addition, it is desirable to provide an apparatus and method which easily provides consistent measurements of permeability, allowing the development of a consistent index of permeability with which to compare structures and sealers at any time. It is preferable that such a method and apparatus be adapted to provide a quality control check so that a structure may be tested as it is erected.

SUMMARY OF THE INVENTION

These and other objects are realized by the present invention, one embodiment of which comprises a method for measuring the water permeability in a concrete structure comprising:

a. pressure sealing a selected length of a borehole in the concrete structure, b. injecting an aqueous medium into the selected length of borehole, c. applying sufficient pressure to the injected aqueous medium and for a time necessary to produce a substantially steady state, measurable flow of the aqueous medium into the concrete structure from the selected length of borehole, d. measuring the steady state flow of aqueous medium, and e. computing from the steady state flow measurement the water permeability of the concrete structure.

A further embodiment of the invention comprises an apparatus for measuring the water permeability in a concrete structure comprising:

a. pressure sealing means to seal a selected length of a borehole in a concrete structure, b. means to inject an aqueous medium into the sealed selected length of borehole, c. means to apply a positive fluid pressure to the injected aqueous medium in the selected length of borehole, and d. means to measure the flow rate of the injected aqueous medium from the selected length of borehole into the concrete structure.

DETAILED DESCRIPTION OF THE INVENTION

The invention provides an expedient and efficient method for the field measurement of the water permeability of concrete structures and a convenient, easy to use, portable apparatus for making the measurements.

Figure 1:
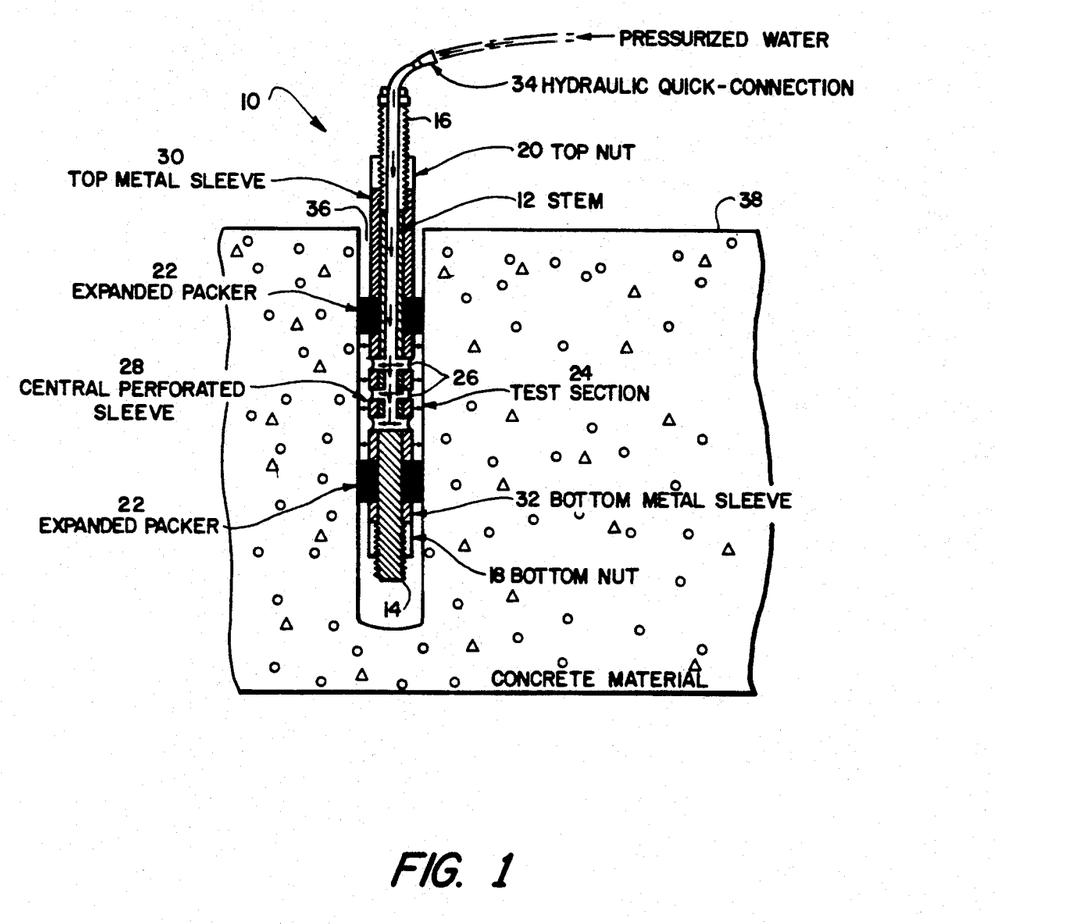
FIG. 1 is a cross-sectional view of an embodiment of the invention.

Referring to FIG. 1, a cross-sectional view of the apparatus of the invention is shown. The apparatus consists of probe 10 which comprises a smooth metal (preferably stainless steel) rod 12 which is externally threaded at its distal 14 and proximal 16 ends to receive nuts 18 and 20, respectively.

Expansible (preferably neoprene) packers 22 surround the rod 12 between the proximal 16 and distal 14 ends to define a test section 24. The rod 12 is hollow from the proximal end to adjacent the packer 22 nearest the distal end 14. Within the test section 24 and between the packers 22, the rod 12 is provided with openings 26 to allow communication between the hollow interior portion of rod 12 and the test section 24. A central sleeve 28, perforated such that the perforations coincide with the opening 26, is positioned around the rod 12 between and communicating with the ends of the packers 22 in test section 24. A top and bottom metal sleeve 30 and 32, respectively, surround rod 12 between the ends of the packers 22 outside the test section 24.

The bottom nut 18 is securely fastened at the distal end 14 of rod 12, thereby preventing downward movement of any portion of the rod 12. The proximal end 16 of the rod 12 is equipped with a hydraulic quick-connect fitting 34 to permit connection of tubes to deliver fluids or create vacuums within the hollow interior of rod 12 and the test section 24 in communication therewith via holes 26.

When the probe 10 is positioned within a borehole 36 in concrete structure 38, the top nut 20 is tightened which compresses and expands packers 22 against sleeves 28, 30 and 32. The packers expand at the same rate, thus sealing off test section 24.

Upon loosening the top nut 20, both packers 22 are simultaneously released and the probe 10 can be easily removed from borehole 36.

Referring to FIGS. 2A-2D, schematic drawings of a flow measurement means in accordance with the invention are shown.

Figure 2A:
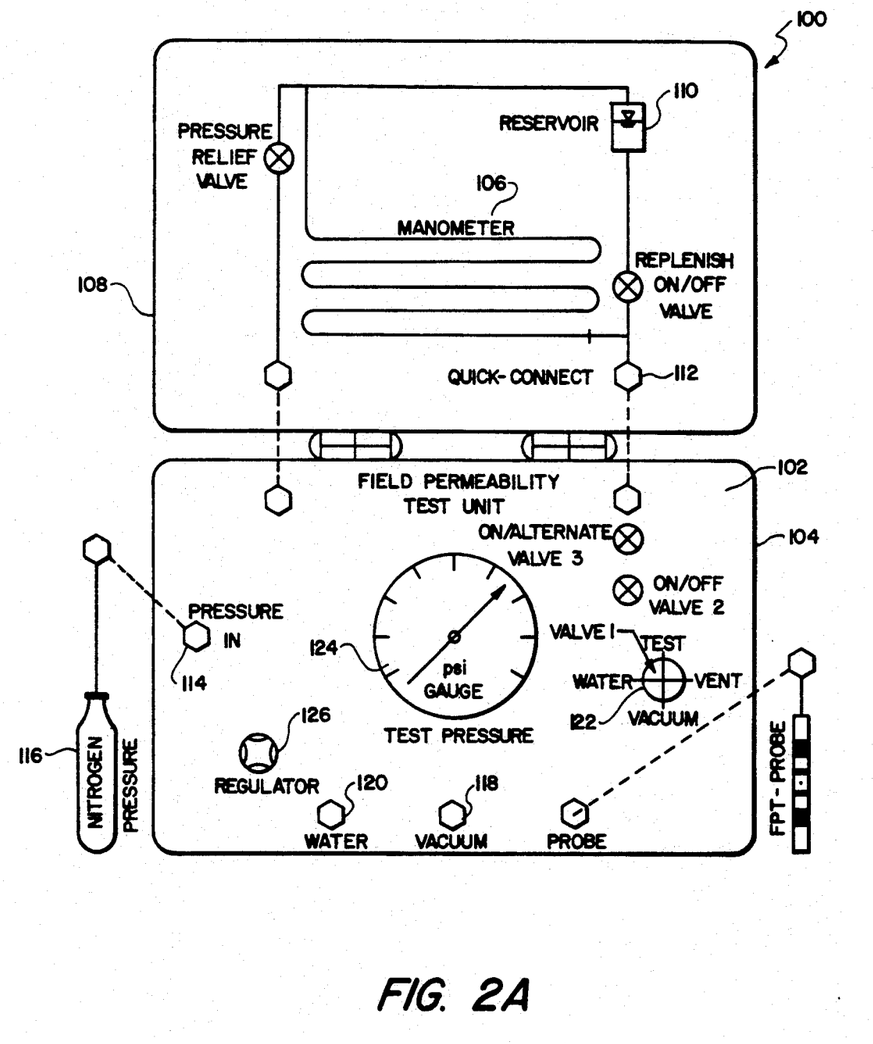
FIGS. 2A-2D are schematic drawings of an embodiment of a flow measurement means in accordance with the present invention.

Referring to FIG. 2A, the FPT control and measurement unit is preferably contained in a carrying case 100 with a central control panel 102 attached to the lower shell 104, and a manometer set-up 106 mounted on the upper shell 108. The upper shell 108 of the carrying case 100 contains a manometer for monitoring of water flow during an FPT and a small high-pressure water reservoir 110 (100 cc) which provides convenient replenishment of water to the manometer for continuous and uninterrupted test runs.

In the running of an FPT, the FPT probe is connected to the central control panel through the hydraulic quick-connection fitting 112. The central control panel also provides quick connections 114 to allow easy connection of an air pressure source 116 (e.g., by means of a portable pressurized nitrogen tank), 118 for a vacuum source (by means of a portable hand-operated vacuum pump) and 120 for a water source (by means of a portable water tank) to the FPT system. A valve switch 122 on the central control panel allows for convenient selection of what is to be connected to the FPT probe. The four selections on the valve switch are (1) pressure release vent, (2) vacuum, (3) water and (4) manometer (or the test position).

Figure 2B:
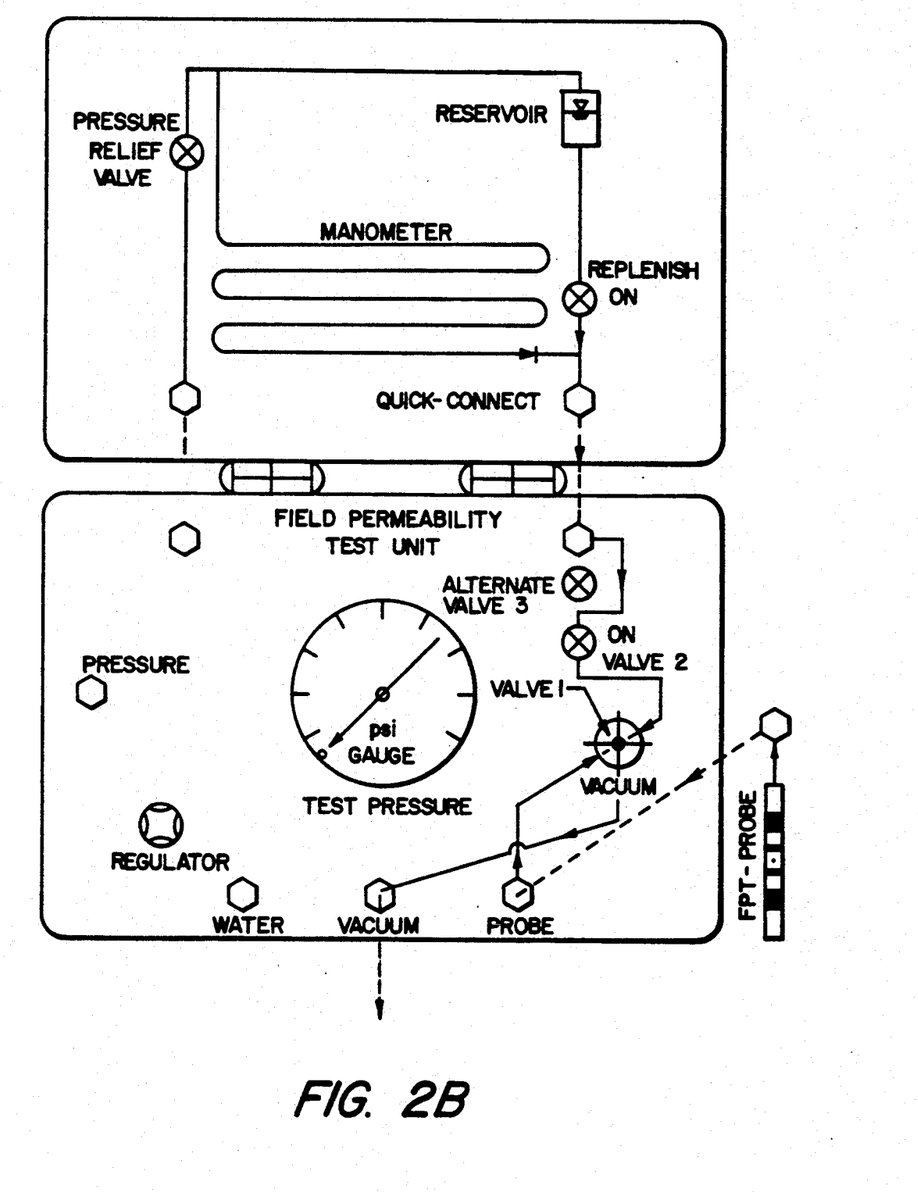

When the valve switch is at the vacuum position, the vacuum source is then channeled to be connected to the FPT probe, which is connected to the central control panel through the quick connection. FIG. 2B shows the interior tube connections at this valve position. At this valve position, the vacuum is also channeled to the manometer tube to pull out the air in the tubing.

Figure 2C:
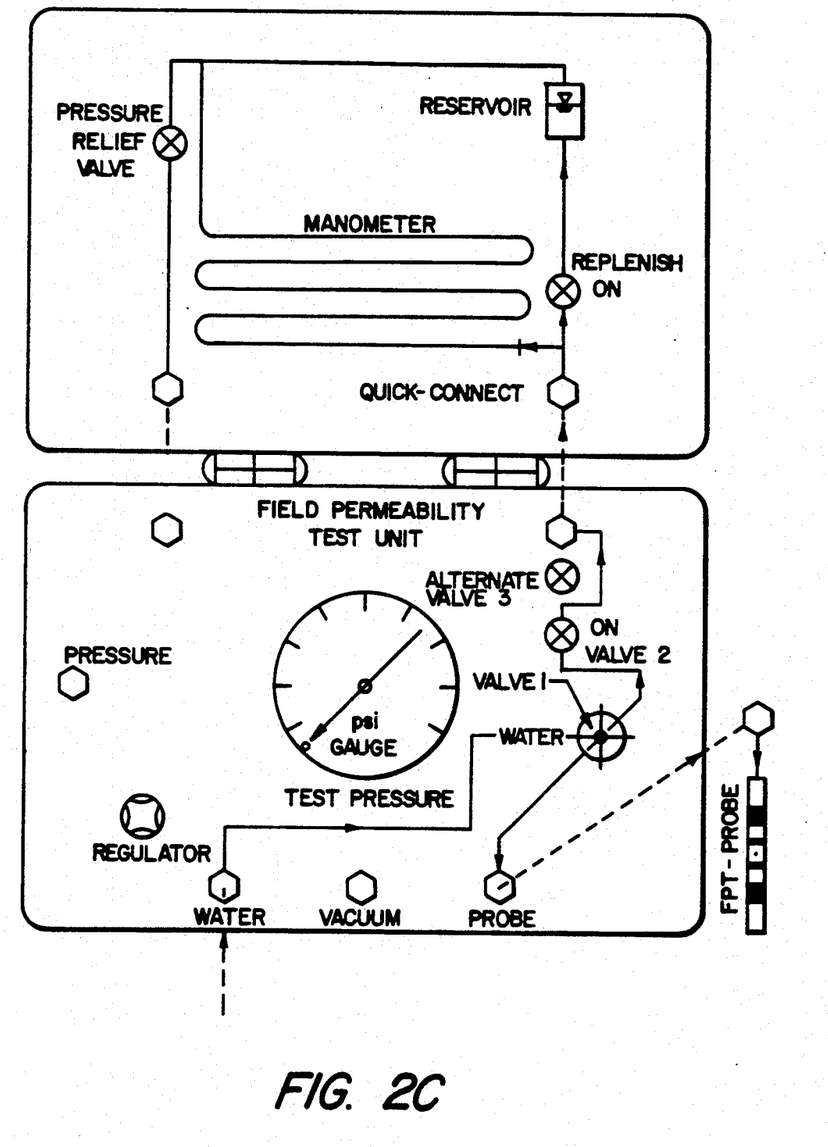

When the valve switch is at the water position, the water source is connected to both the FPT probe and the manometer tube. FIG. 2C shows the interior connections for this setting.

Figure 2D:
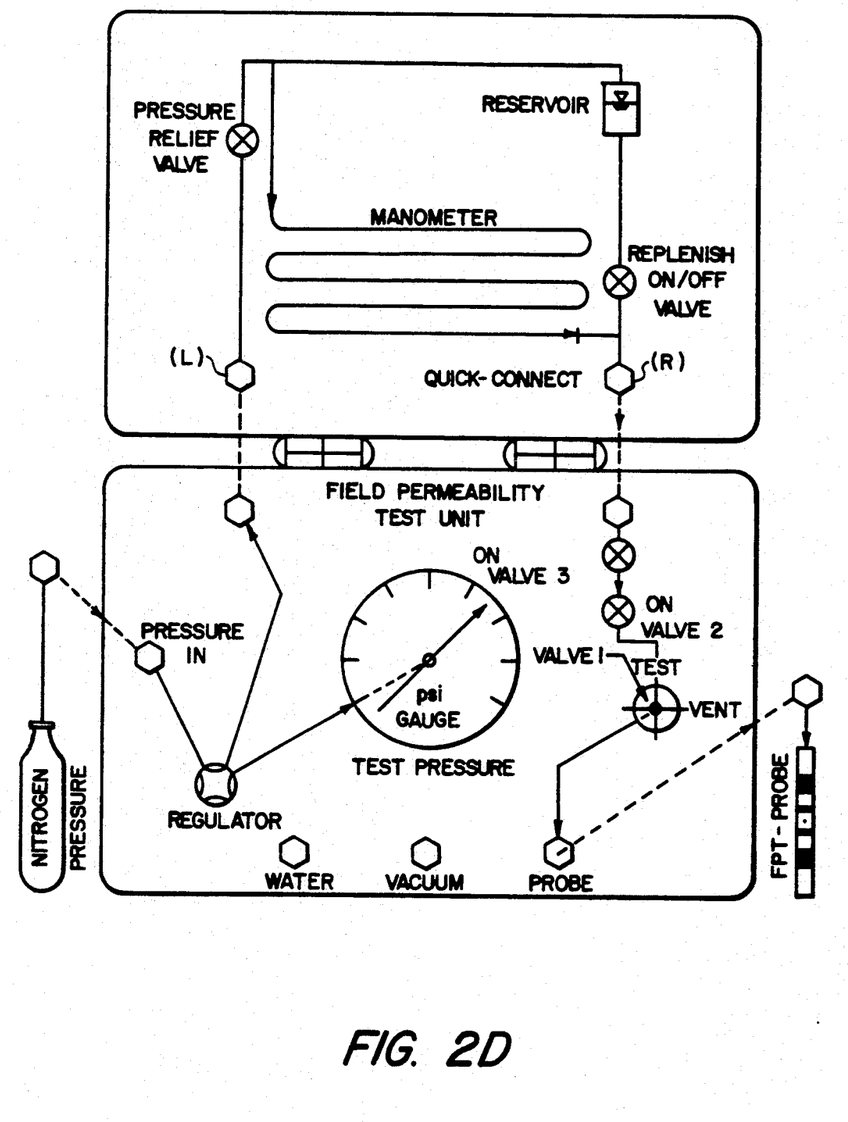

Referring to FIG. 2D, to start the test, the manometer is connected to the pressure channel via the left quick connection (L). The pressurized nitrogen source is connected to the control panel via the "pressure". In quick connection and the valve switch is then turned to the test position. At this valve position, the pressurized water is now channeled to the FPT probe. FIG. 2D shows the interior connections for this setting. The central control panel also contains a high resolution pressure gauge 124 and regulator 126 to allow for convenient control of the applied air pressure to the FPT system.

The preferred aqueous medium for use in connection with testing the permeability of concrete with the method and apparatus of the present invention is water. It will be understood by those skilled in the art, however, that aqueous media containing any of various additives may also be employed for special purposes. For example, the fluid may contain a dye (to observe the flow path of the aqueous medium and to detect micro-cracks), pH indicator, or other agent designed to interact with the concrete such as sodium chloride to determine chloride permeability.

The invention is illustrated by the following non-limiting examples.

EXAMPLE 1

A ⅜-inch diameter, 6-inch deep hole 36 is drilled perpendicular to the concrete surface. The field permeability test (FPT) probe 10 is inserted in the drilled hole 36. The top nut 20 of the probe 10 is tightened to force the double packers 22 to seal off the middle section 24 of the hole 36. A full vacuum (76 cm Hg) is applied to the sealed hole via a tube attached to quick-connect fitting 34 through the FPT probe for 5-10 minutes to remove air from the concrete material and the measuring system. Water is injected into the hole via fitting 34 through the FPT probe.

To begin testing, a pressure of 150-500 psi (1.0 to 3.4 MPa) is applied to the water source to produce a measurable flow. Normally, a 250 psi (1.7 MPa) is used. The flow of water into the concrete mass is measured by means of the water level in the manometer tube. After the pressurized water has been applied for 30 minutes, at which time the flow rate has stabilized, a manometer reading is taken every 5 to 15 minutes, for about 2 hours. Although it is not necessary that the entire length of the borehole be fitted with fluid (only the test section need be constantly filled), keeping the entire length filled will hasten saturation of the concrete and reduce testing time.

The measured steady state flow rate is used to compute the apparent coefficient of permeability by means of the following equations:

$$K = \frac{Q}{2\pi L_o h} \sinh^{-1}\left(\frac{L_o}{2r}\right); \text{ for } r \leq L_o < 10r \tag{1A}$$

and $$K = \frac{Q}{2\pi L_o h} \log_e\left(\frac{L_o}{r}\right); \text{ for } L \geq 10r \tag{1B}$$

wherein:
K = coefficient of permeability
h = applied pressure head
$L_o$ = length of test section
Q = flow rate
r = radius of borehole.

EXAMPLE 2

The developed FPT method was evaluated extensively in the laboratory in order to determine its applicability, reliability and performance characteristics. Concrete blocks with dimensions of 12 inches × 12 inches (30.5 cm × 30.5 cm) × 8 inches (20.3 cm) were cast in the laboratory and moist-cured for 28 days before testing. A 6-inch deep, ⅜-inch diameter hole was drilled in the middle of each block, and tests were run on these concrete blocks using the above-described FPT apparatus and method.

Figure 3:
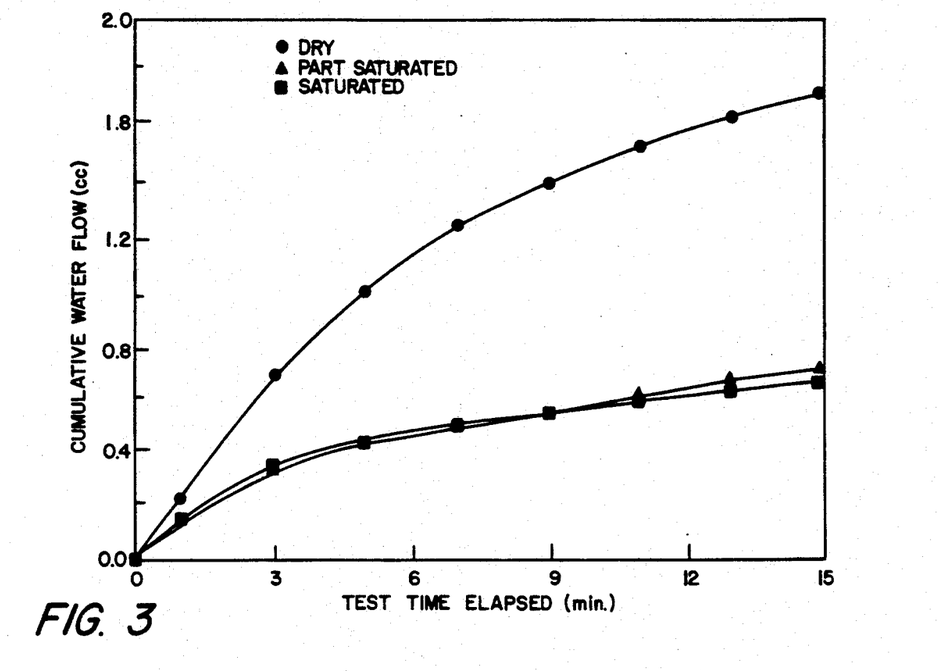
FIGS. 3 and 4 are plots of the results achieved according to the method of the invention as described in Examples 2 and 3, respectively.

The effect of the initial moisture condition of concrete on the FPT flow measurements was investigated by running the FPTs on concrete blocks of three different conditions, i.e., (1) dry, (2) partially saturated and (3) saturated. The first condition was obtained by allowing the concrete block to air-dry in the laboratory for at least one week. Condition (2) was achieved by filling the test hole with water for at least 24 hours prior to testing. Condition (3) was achieved by running an FPT on the concrete block within the last 24 hours. Complete saturation of the test section is defined as saturation to the extent that further saturation will not affect the results of the FPT. FIG. 3 shows the typical water flows measured in the FPTs run on concrete blocks of these three conditions. Generally, a relatively larger water flow was measured for condition (1), while those for conditions (2) and (3) were comparable to one another. Analyses of data obtained from a number of tests indicated that the initial moisture condition of the concrete had a significant effect on the FPT measurements. However, the results also indicated that relatively constant flow rates were obtained if the concrete had been pre-saturated (condition 2) or pre-tested using the FPT device (condition 3). Therefore, a vacuum pre-conditioning and subsequent pre-saturation of the test section prior to testing were adopted as the preferred procedure.

Figure 4:
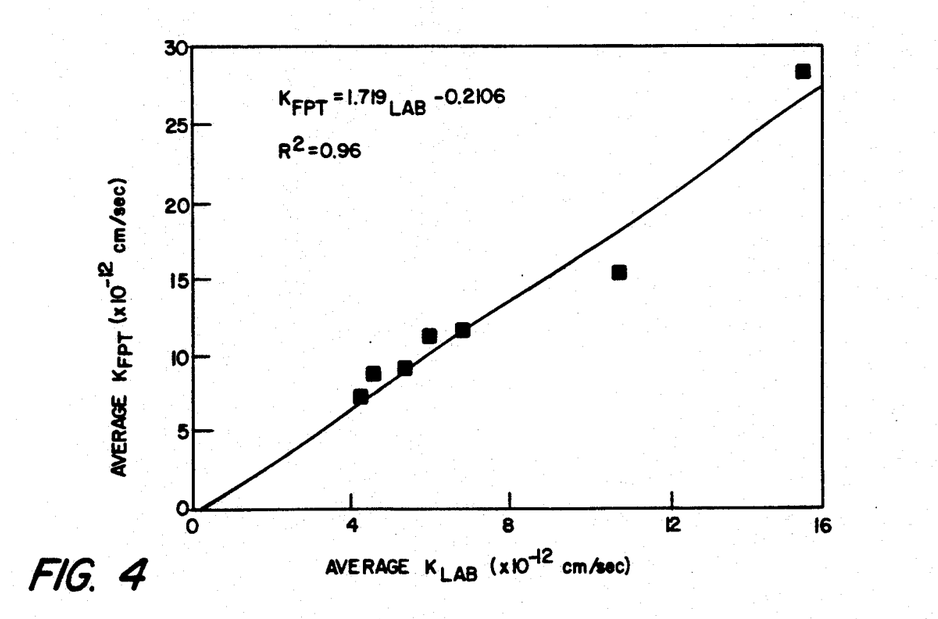

The coefficients of permeability as determined by the FPTs on these concrete blocks were checked with those obtained by an existing laboratory permeability test method which was developed by Soongswang et al and had been shown to produce reliable results [Soongswang et al, Transportation Research Record, Vol. 1204, pp. 71-82 (1988)]. In this laboratory test method, the rate of flow of water through a cylindrical concrete specimen 4 inches (10.2 cm) in diameter and 2 inches (5.1 cm) in height under a pressure of 100 psi (690 kPa) is used to determine the coefficient of permeability by a direct application of Darcy's Law. The laboratory permeability tests were run on concrete specimens made by the same batches of concrete for the concrete blocks, and moist-cured for 28 days. FIG. 4 shows the plot of the average coefficients of permeability as determined by the FPTs, $K_{FPT}$, against the average permeability coefficients as determined by the laboratory method, $K_{LAB}$, for the same batches of concrete. A correlation analysis between the results of the FPT and laboratory test was performed using linear regression. A coefficient of determination ($r^2$) of 0.96 was obtained, indicating that the relation between the two methods is highly significant. The regression equation has a slope of 1.719, as shown in FIG. 4. In consideration of the high variability of most permeability test results, a difference of 70% in permeability coefficient could be regarded as minimal. The closeness of the FPT results to the laboratory permeability test results indicated that the FPT method produces consistent and reliable test results.

The FPTs were also run on the concrete blocks with the FPT probe placed at different test orientations (horizontal, vertical, etc.). The results indicated that test orientation had no significant effects on the FPT test results.

EXAMPLE 3

The performance and reliability of the developed FPT apparatus and method were evaluated in numerous field testing operations carried out on in-service concrete structures throughout Florida. A total of thirteen concrete bridge structures were tested using the developed FPT apparatus. FPTs were performed on structural elements such as pile columns, piers, pier/pile cups, bascules, etc., of bridge sub-structures, at various locations, elevations and orientations. Flow measurements were remotely taken by means of the FPT instrumentation unit which was carried on and operated from a boat. The FPTs were conducted by one person plus an assistant, and test measurements were completed usually within two hours from the commencement of the actual test run. The entire FPT operation including coring, pre-conditioning, testing and patching of concrete was completed within approximately two to three hours. The FPT apparatus demonstrated satisfactory performance and no major problems were encountered in any of the field installations.

A sample of the data obtained from the on-going field testing program employing the developed FPT is shown in Table 1. Repetitive FPTs performed at the same test locations on this particular bridge structure produced results having a percent variation ranging from about 4% to about 28%, indicating that the FPT method demonstrates acceptable repeatability.

TABLE 1

| SAMPLE OF FPT RESULTS | | | |
|---|---|---|---|
| Structural Element | Location | Pressure (psi) | Computed Apparent K ($10^{-10}$ in/sec) |
| Offshore Pile | #1 | 500 | 3.9 |
| " | #1 Repeat | 500 | 3.7 |
| " | #2 | 250 | 18.0 |
| " | #2 Repeat 1 | 250 | 15.3 |
| " | #2 Repeat 2 | 250 | 14.0 |
| " | #3 | 250 | 18.6 |

TABLE 1-continued

| SAMPLE OF FPT RESULTS | | | |
|---|---|---|---|
| Structural Element | Location | Pressure (psi) | Computed Apparent K ($10^{-10}$ in/sec) |
| " | #3 Repeat | 250 | 17.8 |
| Onshore Pile | #4 | 500 | 16.4 |
| " | #4 Repeat 1 | 500 | 14.4 |
| " | #4 Repeat 2 | 500 | 13.7 |

Note:
FPTs were performed at B. B. McCormick Bridge, Jacksonville, Florida
1 in/sec = 2.54 cm/sec
1 psi = 6895 N/m$^2$

We claim:

1. A method for measuring the water permeability in a concrete structure comprising:
   a. pressure sealing a selected length of a borehole in said concrete structure,
   b. injecting an aqueous medium into said selected length of borehole,
   c. applying sufficient pressure to said injected aqueous medium and for a time necessary to produce a substantially steady state, measurable flow of said aqueous medium into said concrete structure from said selected length of borehole, said borehole having been pre-conditioned with said aqueous medium before said pressure sealing of a selected length thereof to saturate the concrete structure surrounding said borehole such that, upon application of pressure in step c to said aqueous medium, said steady state flow thereof is substantially instantly produced,
   d. measuring said steady state flow of aqueous medium, and
   e. computing from said steady state flow measurement the water permeability of said concrete structure.

2. The method of claim 1 wherein said aqueous medium is water.

3. The method of claim 1 including the preliminary step of boring said hole of selected length in said concrete structure.

4. The method of claim 1 wherein a full vacuum is applied to said selected length of borehole prior to said injecting of said aqueous medium.

5. The method of claim 1 wherein said flow of aqueous medium from said borehole into said concrete structure is measured by means of a water manometer.

6. The method of claim 1 wherein said water permeability of said concrete structure is computed as the coefficient of permeability, K, by means of one of the following equations:

$$K = \frac{Q}{2\pi L_o h} \sinh^{-1}\left(\frac{L_o}{2r}\right); \text{ for } r \leq L_o < 10r$$

and $$K = \frac{Q}{2\pi L_o h} \log_e\left(\frac{L_o}{r}\right); \text{ for } L \geq 10r$$

wherein:
K = coefficient of permeability
h = applied pressure head
$L_o$ = length of test section
Q = flow rate r = radius of borehole.

7. Apparatus for measuring the water permeability in a concrete structure comprising:
   a. pressure sealing means to seal a selected length of a borehole in a concrete structure,
   b. means to inject an aqueous medium into said sealed selected length of borehole,
   c. means to apply a positive fluid pressure to said injected aqueous medium in said selected length of borehole,
   d. means to measure the flow rate of said injected aqueous medium from said selected length of borehole into said concrete structure, and
   e. means to compute the water permeability of said concrete structure as the coefficient of permeability by one of the following equations:

$$K = \frac{Q}{2\pi L_o h} \sinh^{-1}\left(\frac{L_o}{2r}\right); \text{ for } r \leq L_o < 10r$$

and $$K = \frac{Q}{2\pi L_o h} \log_e\left(\frac{L_o}{r}\right); \text{ for } L \geq 10r$$

wherein:
K = coefficient of permeability
h = applied pressure head
$L_o$ = length of test section
Q = flow rate
r = radius of borehole.

8. An apparatus according to claim 7, wherein said flow rate measuring means is a water monometer.

9. An apparatus according to claim 7 wherein said pressure sealing means is equipped with a hydraulic quick-connect fitting by which said means to inject said aqueous medium into said selected length of borehole can be quick-connected and -disconnected.

10. An apparatus according to claim 9 wherein said flow rate measuring means is quick-connectable to and -disconnectible from said hydraulic quick-connect fitting.

11. An apparatus according to claim 9 also including means to apply a positive air pressure to said selected length of borehole, said means being quick-connectable to and -disconnectible from said hydraulic quick-connect fitting.

12. An apparatus according to claim 9 also including means to create a vacuum in said selected length of borehole and in said measuring means, said means being quick-connectible to and -disconnectible from said hydraulic quick-connect fitting.

13. An apparatus according to claim 9 also including valve means to maintain the contents of and pressure in said selected length of borehole during quick-connection and -disconnection of said hydraulic quick-connect fitting.

14. An apparatus according to claim 7 wherein said pressure sealing means comprises straddle packer means.

15. A method for measuring the water permeability in a concrete structure comprising:
   a. pressure sealing a selected length of a borehole in said concrete structure,
   b. applying a full vacuum to said selected length of borehole;
   c. injecting an aqueous medium into said selected length of borehole,
   d. applying sufficient pressure to said injected aqueous medium and for a time necessary to produce a substantially steady state, measurable flow of said aqueous medium into said concrete structure from said selected length of borehole,
   e. measuring said steady state flow of aqueous medium, and
   f. computing from said steady state flow measurement the water permeability of said concrete structure.

16. A method for measuring the water permeability in a concrete structure comprising:
   a. pressure sealing a selected length of a borehole in said concrete structure,
   b. injecting an aqueous medium into said selected length of borehole,
   c. applying sufficient pressure to said injected aqueous medium and for a time necessary to produce a substantially steady state, measurable flow of said aqueous medium into said concrete structure from said selected length of borehole,
   d. measuring said steady state flow of aqueous medium, and
   e. computing from said steady state flow measurement the water permeability of said concrete structure as the coefficient of permeability, K, by means of one of the following equations:

$$K = \frac{Q}{2\pi L_o h} \sinh^{-1}\left(\frac{L_o}{2r}\right); \text{ for } r \leq L_o < 10r$$

and $$K = \frac{Q}{2\pi L_o h} \log_e\left(\frac{L_o}{r}\right); \text{ for } L \geq 10r$$

wherein:
K = coefficient of permeabilty
h = applied pressure head
$L_o$ = length of test section
Q = flow rate
r = radius of borehole.

* * * * *

UNITED STATES PATENT AND TRADEMARK OFFICE
CERTIFICATE OF CORRECTION

PATENT NO. :   5,219,388
DATED      :   June 15, 1993
INVENTOR(S):   Constantinos A. MELETIOU, ET AL It is certified that error appears in the above-identified patent and that said Letters Patent is hereby corrected as shown below:

Column 8, line 46 [claim 4, line 3]: delete "injecting" and insert -- injection --.

Column 9, line 35 [claim 8, line 2]: delete "monometer" and insert -- manometer --.

Column 10, line 52 [claim 16, line 22]: delete "permeabilty" and insert -- permeability --.

Signed and Sealed this

First Day of February, 1994

Attest:

BRUCE LEHMAN

*Attesting Officer*   *Commissioner of Patents and Trademarks*